United States Patent [19]

Gordon et al.

[11] Patent Number: 4,493,705
[45] Date of Patent: Jan. 15, 1985

[54] BLOOD RESERVOIR

[75] Inventors: Lucas S. Gordon; Jeanne Pierson, both of Irvine, Calif.

[73] Assignee: Bentley Laboratories, Inc., Los Angeles, Calif.

[21] Appl. No.: 406,962

[22] Filed: Aug. 10, 1982

[51] Int. Cl.³ .................... A61M 1/03; B01D 19/02
[52] U.S. Cl. ........................... 604/122; 604/4; 604/406; 128/DIG. 3; 55/364; 210/927
[58] Field of Search .......... 604/4, 7, 408, 406, 604/410, 190, 252, 122, 251; 128/DIG. 3; 210/927, 321.3, 436, 456, 472; 55/364, 372, 378, 159

[56] References Cited

U.S. PATENT DOCUMENTS

| | | | |
|---|---|---|---|
| 1,923,846 | 8/1933 | Roig | 604/415 |
| 3,554,256 | 6/1971 | Anderson | 604/408 X |
| 3,827,860 | 8/1974 | Burlis | 128/DIG. 3 |
| 4,026,669 | 5/1977 | Leonard et al. | 604/4 X |
| 4,035,304 | 7/1977 | Watanabe | 604/406 X |
| 4,164,468 | 8/1979 | Raible | 210/436 X |
| 4,344,777 | 8/1982 | Siposs | 210/436 X |
| 4,368,118 | 1/1983 | Siposs | 210/436 X |
| 4,428,743 | 1/1984 | Heck | 604/251 |

Primary Examiner—C. Fred Rosenbaum
Assistant Examiner—Michelle N. Lester
Attorney, Agent, or Firm—Lyon & Lyon

[57] ABSTRACT

A yoke shaped collapsible blood reservoir having first and second yoke legs joined by a yoke midsection. A filter element is positioned in the yoke midsection and across the blood flow path between an inlet at the base of the first yoke leg and a blood outlet at the base of the second yoke leg. An angular blood inlet and a gradual increase in cross-sectional area from the blood inlet to the yoke midsection decreases turbulence and assists in bubble separation.

10 Claims, 2 Drawing Figures

BLOOD RESERVOIR

BACKGROUND OF THE INVENTION

1. Field of the Invention

The present invention relates to a collapsible blood reservoir for use in a cardiopulmonary bypass system.

2. Description of the Prior Art

Generally, a cardiopulmonary bypass system is a medical system used in cardiovascular surgery, intensive care and surgical recovery that is coupled to a human body to revitalize and pump blood, thereby performing certain functions of the heart and lungs and often partially or fully bypassing a portion of the circulatory system. The cardiopulmonary bypass system receives a venous blood feed (oxygen deficient blood) from the human circulatory system, oxygenates and typically transfers heat with the blood and returns the blood to the circulatory system at a flow rate approximately corresponding to the venous drainage, thus reducing the load on the lungs and heart.

A cardiopulmonary bypass system in a partial support capacity is used, for example, during cardiac intensive care of patients who have suffered a cardiac infarction where a portion of the heart muscle has died from an insufficient blood supply. The dead muscle is soft and difficult to suture since it will tear easily. The muscle may heal if the patient is kept quiet and heart chambers are subject to a minimum amount of pressure. Failing such care, an aneurysm may result in which the softened muscle swells up and stagnates pools of blood which tend to clot. The tendency toward development of an aneurysm is minimized reducing the pumping load on the heart with the partial support system. Typically the infarcted tissue scars over and thereby regains its tensile integrity in several weeks during which time the cardiopulmonary bypass system must operate continuously. Recent developments in pump oxygenation equipment, such as membrane oxygenators having limited long term blood degradation effects, have made possible long term partial support of this duration.

Many specific requirements must be met in a practical partial support system. For example, the cardiopulmonary bypass system experiences a load as the blood is returned to the human body. The load is variable and the flow impedance seen by the cardiopulmonary bypass system may increase if, for example, the arteries are constricting or decrease when hemorrhaging is occurring. Yet the cardiopulmonary bypass system should generally maintain a constant flow rate to the human body, equal to the venous drainage.

The rate and changes in rate of blood flow indicates the physical state of the patient, and thus it would be desirable to monitor the blood flow rate. The physician may find it necessary to increase or decrease the return flow rate of the blood. Increasing the blood flow rate in excess of the drainage rate often requires the addition of blood to the system. It would be advantageous to have a cardiopulmonary bypass system which could introduce quantities of blood to the blood flow in addition to the blood supplied by the patient's circulatory system.

The quantity of blood flowing in the circulatory system of a young infant is extremely critical. For example, hyaline membrane disease attacks the alveolar sacks of infants. When this occurs, the lining of the lungs is impervious to oxygen and $CO_2$. Since the infant having this disease receives insufficient oxygen, the treatment in the past has been to increase, in concentration and pressure, the oxygen provided to the infant. Although the disease is often cured by this technique, other serious conditions may set in which are caused by the toxic effects of oxygen such as retrolental fibroplasia, in which the retina is destroyed. By using a cardiopulmonary bypass system, the lungs are allowed to heal. The control of blood volume is extremely important since the hyaline disease typically occurs with underweight infants, typically less than 2500 grams and having a total blood volume of only 150-300 cc.

Thus, it would be desirable to have a cardiopulmonary bypass system that is safe, reliable and volume alterable.

SUMMARY OF THE INVENTION

A generally yoke or inverted "U" shaped collapsible blood reservoir. The yoke midsection joins first and second yoke legs and is in fluid communication therewith. A vent is provided at the uppermost part of the yoke midsection and an angular blood inlet and a gradual increase in reservoir cross-sectional area from the blood inlet to the yoke midsection decreases turbulence and assists in bubble separation. A filter element, having a pore size of between about 100 and 250 microns is positioned in the yoke midsection. Preferably the ratio of the height of the reservoir chamber to the height of the center of the yoke midsection is between about 1.7 and 1.2.

DETAILED DESCRIPTION OF PREFERRED EMBODIMENTS

Figure 1:
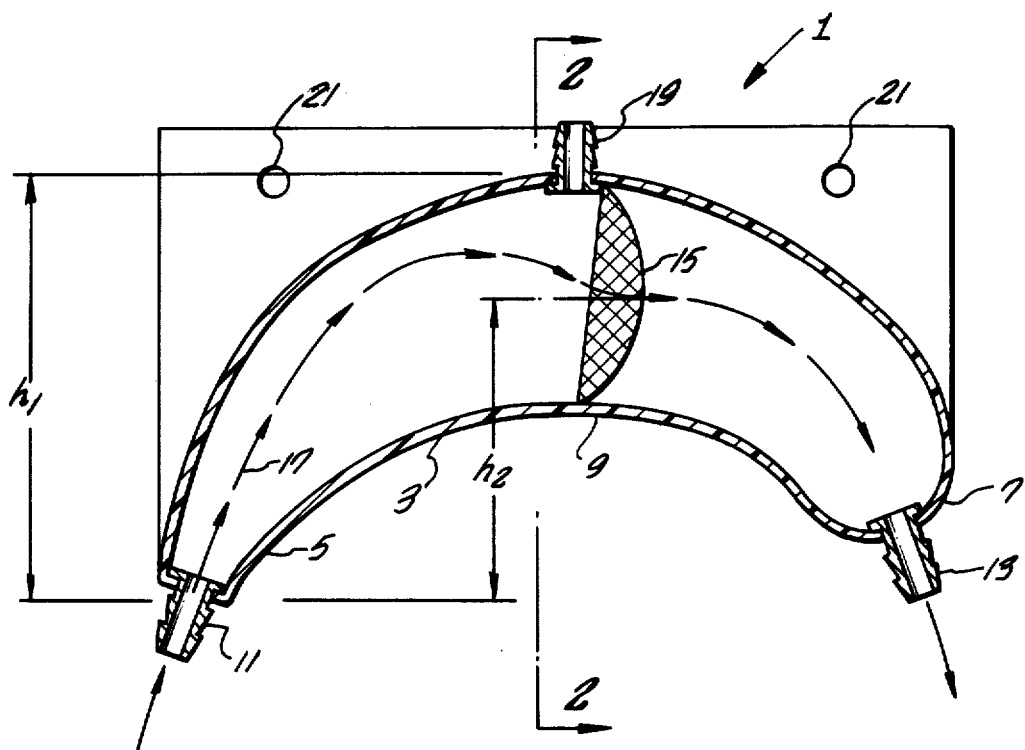
FIG. 1 is a cross-sectional view of the present invention.
Figure 2:
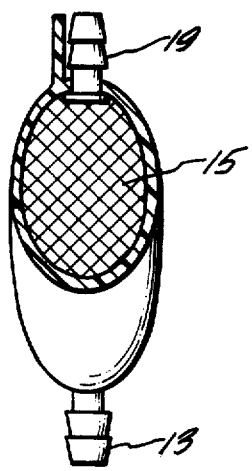
FIG. 2 is a cross-sectional view taken about 2—2 of FIG. 1.

Referring to FIG. 1, in a preferred embodiment blood reservoir 1 includes a yoke shaped reservoir chamber 3 and a support member 23 having apertures 21 therein suitable for hanging the device from a stand. Yoke shaped reservoir chamber 3 includes a first yoke leg 5 and a second yoke leg 7 joined by, and in fluid communication with, a yoke midsection 9. The yoke shaped reservoir chamber is preferably collapsible and flexible such that the chamber will collapse as fluid is withdrawn thereby preventing gas bubbles from passing out through outlet 13.

Blood inlet 11 is provided in the first yoke leg 5 and blood outlet 13 is positioned in the second yoke leg 7. In a preferred embodiment the centerline of the blood inlet 11 and blood outlet 13 are positioned at an upward angle with respect to the centerline of the yoke leg 5, 7 centerlines, respectively, such that the angle between the centerline of the blood inlet 11 and blood outlet 13 and horizontal is between about 30° and about 60°.

Further, the cross-sectional area of the reservoir chamber 3 is such that it increases gradually from tapered blood inlet 11 toward the yoke midsection 9 and then gradually decreases toward tapered blood outlet 13. Such an angular blood inlet 11 and gradual cross-sectional area increase toward the yoke midsection 9 decrease turbulence within the blood reservoir 1 and assists in bubble separation. A vent 19 is provided at the approximate uppermost portion of yoke midsection 9 to allow for the venting of such separated gases. The ratio of the height of the reservoir chamber 3 ($h_1$) to the height of the center of the yoke midesection 9 (h₂) is preferably between about 1.7 and about 1.2. In a further preferred embodiment the ratio of the height to the width of the reservoir chamber 3 is less than 1.0 so that a relatively large volume of fluid can be reservoired by the reservoir chamber 3 without a correspondingly large hydraulic head.

A filter means 15 is provided within the yoke midsection 9 and across blood flow path 17. Filter means 15 is preferably one having a pore size of between about 100 and 250 microns. The blood reservoir 1 is preferably formed from flexible thin walled polyvinylchloride, polyurethane or polyethylene plastic material such that the yoke shaped blood reservoir chamber 3 will expand and collapse as the rate of incoming blood increases and decreases, respectively. The yoke shaped blood reservoir 3 is sufficiently flexible such that when the operative use of the blood reservoir 1 is drawing to a close, first yoke leg 3 may be grasped and elevated so that it is above the yoke midsection 9 thereby forcing the remaining reservoired blood to pass through filter means 15 and out through blood outlet 13.

While the invention has been particularly shown and described, and with reference to certain preferred embodiments thereof, it will be understood by those skilled in the art that various changes in form and details without departing from the spirit and scope of the invention.

What is claimed:

1. A blood reservoir comprising:
   a substantially inverted U shaped reservoir chamber having first and second U legs joined by a U midsection;
   a substantially cylindrical inlet at the base of said first U leg said inlet aligned such that its centerline projects upwardly from the centerline of said first U leg;
   an outlet at the base of said second U leg; and a vent at the uppermost portion of the U midsection.

2. The blood reservoir claimed in claim 1 wherein said reservoir further includes a filter element at said U midsection and positioned across the blood flow path between said blood inlet and said blood outlet said filter element is more particularly defined as having a pore size of between about 100 microns to about 250 microns.

3. The blood reservoir in claim 1 wherein said substantially inverted U shaped reservoir chamber is made from plastic.

4. The blood reservoir claimed in claim 1 wherein the ratio of the height of the reservoir chamber to the height of the center of the U midsection is between about 1.7 and about 1.2.

5. A flexible collapsible blood reservoir comprising:
   a substantially U shaped reservoir chamber having first and second U legs joined by a U midsection wherein the ratio of the height of the reservoir chamber to the height of the center of the U midsection is between about 1.7 and about 1.2;
   a blood inlet at the base of said first U leg;
   a blood outlet at the base of said second U leg;
   a non-flexible filter element positioned at the U midsection and across the blood flow path between said blood inlet and said blood outlet; and
   a vent at the uppermost portion of the U midsection.

6. The blood reservoir claimed in claim 5 wherein said filter element is more particularly defined as having the pore size between about 100 microns to about 250 microns.

7. The blood reservoir claimed in claim 5 wherein said substantially U shaped reservoir chamber is made from polyvinylchloride, polypropoleane or polyurethane.

8. A flexible collapsible blood reservoir comprising:
   a substantially U shaped reservoir chamber having first and second U legs joined by a U midsection, the cross-sectional area of said U being greatest at the U midsection and gradually decreasing toward each U leg base;
   a filter element positioned at the U midsection and across the blood flow path between said blood inlet and said blood outlet; and
   a vent at the uppermost portion of the U midsection.

9. The blood reservoir claimed in claim 8 wherein said filter element is more particularly defined as having a pore size of between about 100 microns to about 250 microns.

10. The blood reservoir claimed in claim 8 wherein the ratio of the height of the reservoir chamber to the height of the center of the U midsection is between about 1.7 and about 1.2.

* * * * *